United States Patent
Shetty et al.

[11] Patent Number: 5,443,510
[45] Date of Patent: Aug. 22, 1995

[54] POROUS COATED IMPLANT AND METHOD OF MAKING SAME

[75] Inventors: H. Ravindranath Shetty; Clarence M. Panchison, both of Warsaw, Ind.

[73] Assignee: Zimmer, Inc., Warsaw, Ind.

[21] Appl. No.: 43,456

[22] Filed: Apr. 6, 1993

[51] Int. Cl.⁶ ............................................. A61F 2/28
[52] U.S. Cl. ......................................... 419/2; 623/23; 623/901; 623/16
[58] Field of Search ............... 623/16, 66, 901, 23; 606/70, 76, 151; 427/2; 433/201.1

[56] References Cited

U.S. PATENT DOCUMENTS

| | | | |
|---|---|---|---|
| 4,636,219 | 1/1987 | Pratt et al. | 623/18 |
| 4,943,412 | 7/1990 | Bania et al. | 420/420 |
| 4,969,904 | 11/1990 | Koch et al. | 623/16 |
| 4,976,738 | 12/1990 | Frey et al. | 623/16 |
| 4,980,127 | 12/1990 | Parris et al. | 420/418 |
| 5,198,308 | 3/1993 | Shetty et al. | 623/16 |

*Primary Examiner*—Paul B. Prebilic
*Attorney, Agent, or Firm*—Todd A. Dawson

[57] ABSTRACT

The method forms a thin layer of metal mesh on the surface of the implant for the bonding with a porous surface layer to prevent the formation of notches within the body of the implant. The layer of metal mesh can be formed by a number of known methods including conventional welding processes such as arc welding, resistance welding, electron beam welding, laser beam welding, friction welding, ultrasonic welding, cladding. The porous metal surface layer is preferably formed from titanium wire or titanium beads in a known process. The porous surface layer is bonded by a known process such as diffusion bonding, sintering, welding, or cladding.

By bonding the porous surface layer to the thin layer of metal mesh, notches normally formed in the body of the implant are substantially eliminated. Therefore, the designer of the implant is not limited as to the location and amount of porous surface layer to be placed on the implants.

11 Claims, 2 Drawing Sheets

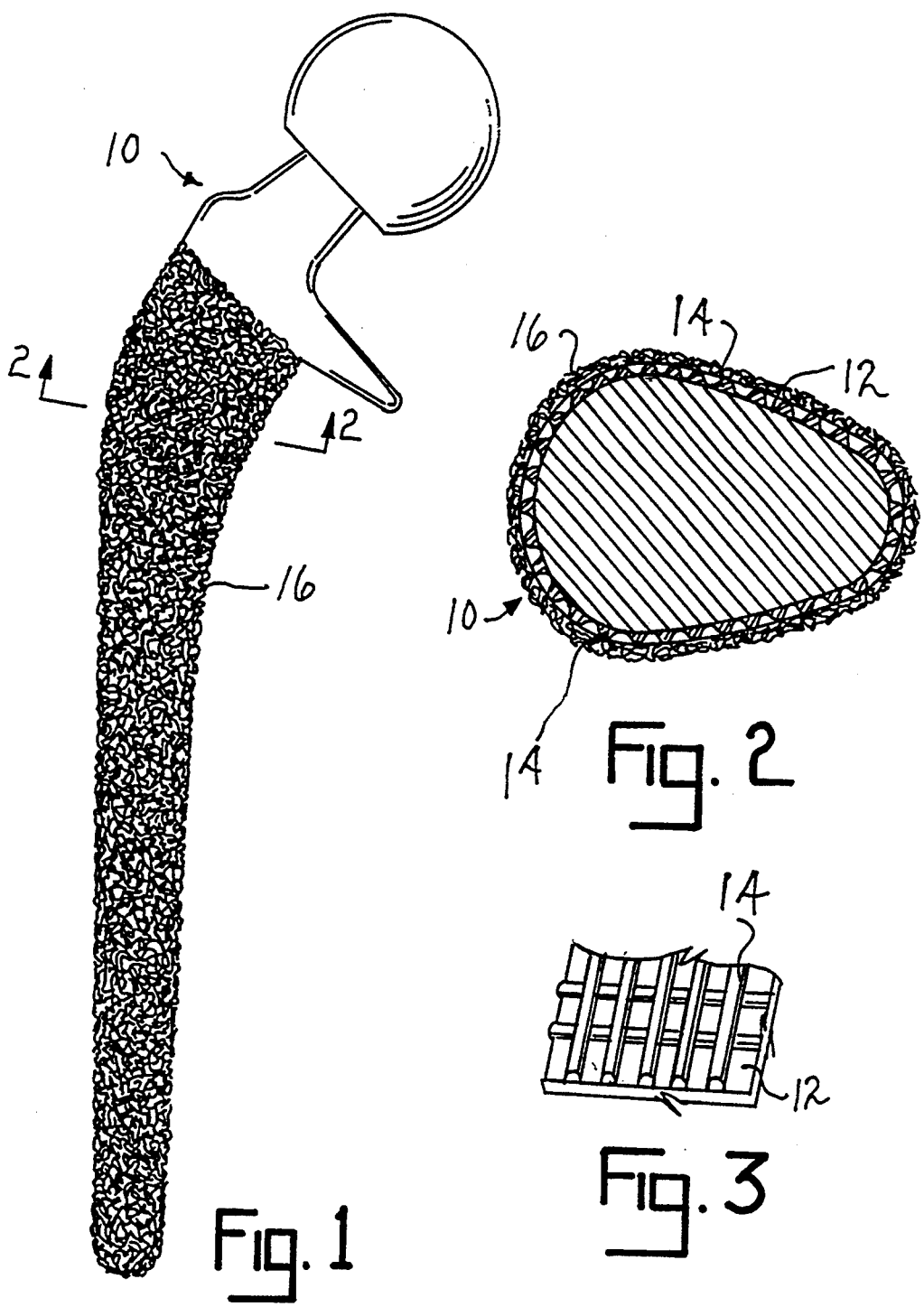

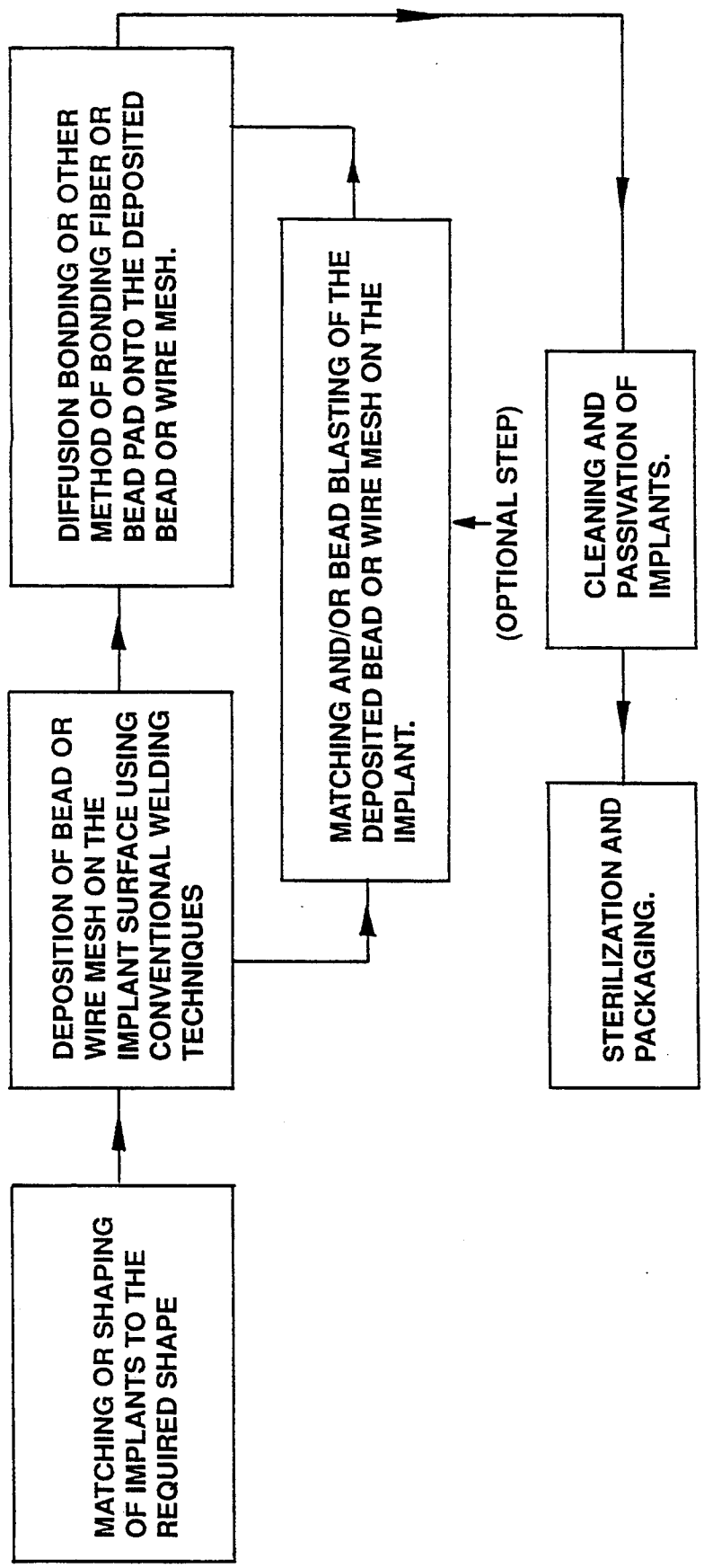
FIGURE 4. PROCESS FLOWCHART

POROUS COATED IMPLANT AND METHOD OF MAKING SAME

FIELD OF THE INVENTION

This invention relates to prosthetic implant having a porous surface attached thereto and has specific relevance to a method of attaching a porous layer to an orthopaedic implant.

BACKGROUND OF THE INVENTION

Prosthetic implants for the replacement of a portion of a patient's joints are well known. Likewise, it is well known to provide a porous surface layer on the implant to promote the ingrowth of bone and enhance fixation of the implant within the bone. The porous surface layer may take the form of a plurality of small beads or a wire mesh. Commonly, the porous surface layer is sintered or diffusion bonded to the implant. Sintering or diffusion bonding requires that the implant and porous surface layer be heated to a temperature sufficient to cause the porous surface layer and implant body to fuse, melt, or bond together at their point of mutual contact. If the sintered or diffusion bonded junctions were viewed in cross section, a small notch would be seen extending into the implant on each side of a contact point between the porous surface layer and the implant. These notches decrease the mechanical strength of the implant. To compensate for the effect of the notches and maintain the strength of the implant above the minimum guidelines established by the FDA of 18.9 ksi, the prosthetic implant manufacturer designs the implant to ensure that the resultant strength is well above the established minimum after bonding. This may require the porous surface layer be limited only to areas of large cross sections to meet the design strength criterion. This may limit the manufacturer in the ability to place porous surface layers on smaller sized implants having smaller cross sections.

SUMMARY OF THE INVENTION

The method and implant of this invention solves the problems discussed above by creating a thin layer of metal mesh on the surface of the implant and the bonding the porous surface layer onto the mesh. The layer of metal mesh can be formed by a number of known methods including conventional welding processes such as arc welding, resistance welding, electron beam welding, laser beam welding, friction welding, ultrasonic welding, cladding. The thin layer of metal mesh is preferably formed from a beta titanium alloy. The porous metal surface layer is preferably formed from titanium wire or titanium beads in a known process. The porous surface layer is bonded by a known process such as diffusion bonding, sintering, welding, or cladding.

By bonding the porous surface layer to the thin layer of metal mesh, notches normally formed in the body of the implant are substantially eliminated. Therefore, the designer of the implant is not limited as to the location and amount of porous surface layer to be placed on the implants.

Accordingly, it is an advantage of the invention to provide a novel method for attaching a porous surface layer to an implant body which limits the formation of notches in the body.

Another advantage of the invention is to provide for a novel implant having a porous metal surface layer connected to an metal mesh formed on an implant body.

Another advantage of the invention is to provide for a method of bonding a porous surface layer to an orthopaedic implant.

Other advantages will become apparent upon a reading of the following description taken with the accompanying drawings.

BRIEF DESCRIPTION OF THE DRAWINGS

FIG. 1 is an elevational view of a hip stem having a porous coat attached thereto in keeping with the invention.

FIG. 2 is a cross sectional view taken along line 2—2 of FIG. 1.

FIG. 3 is a perspective view enlarged of a preferred pattern of metal mesh formed on the outer surface of the implant.

FIG. 4 is a flow diagram for the method of the invention.

DESCRIPTION OF THE PREFERRED EMBODIMENT

The preferred embodiments herein described are not intended to be exhaustive or to limit the invention to the precise forms disclosed. Rather, they are chosen and described to best explain the invention so that others skilled in the art might utilize its teachings.

Initially, it is considered advantageous to identify and define terms in the specification to eliminate uncertainty in the mind of the reader.

Metal mesh is used to define a mesh of a predetermine pattern formed from a plurality of intersecting metal weld beads formed on the surface of the implant substrate.

Porous surface layer is used to define a layer of porous material such as fiber metal or beads which have been formed into a pad and are metallurgically bonded to the metal mesh.

Beta titanium alloy identifies preferably, Ti—15-Mo—2 8Nb—O—2Si—3Al, Ti—15Mo—2 8Nb—O 2Si or any other commercially available beta titanium alloy.

Referring now to the flow chart of FIG. 4, to construct an implant in accordance with the invention, a titanium metal mesh preferably of 0.011 inch in cross section is applied to the implant surface. The layer of metal mesh can be formed by forming a plurality of intersecting elongate metal beads from a number of known methods including conventional welding processes such as arc welding, resistance welding, electron beam welding, laser beam welding, friction welding, ultrasonic welding, cladding or similar metallurgical bonding techniques. Preferably the implant is formed from titanium or a titanium alloy. After the wire mesh is deposited upon the implant surface the metal mesh and implant are dry-blasted or shot-peened with metal or ceramic media. Bead blasting of the metal mesh will help in reducing stress concentration at the metal mesh/implant interface. The stress concentration is reduced or eliminated by changing the morphology of any notches formed at the interface between the metal mesh and the implant. Next the porous surface layer of a predetermined thickness is bonded to the metal mesh with a known method such as diffusion bonding. By bonding the porous surface layer to the metal mesh, the amount of notches formed in the implant is reduced and thereby the overall strength of the implant is increased.

This permits the implant to have an increased surface area covered by the porous surface layer.

The preferred embodiments of hip and knee prostheses are illustrated in FIGS. 1 and 2. As illustrated, the metal mesh 14 is formed on the surface 12 of implant 10. Porous surface layer 16 is metallurgically bonded to the metal mesh 14, spaced from the surface 12 of the implant.

In the preferred embodiment the implant is formed from a high strength titanium or titanium alloys, the metal mesh is preferably beta titanium alloy. The porous surface layer may be formed from commercially pure titanium, Ti—6Al—4v alloy, or various beta titanium alloys. The use of beta titanium as the metal mesh on a Ti—6Al—4V alloy implant body will help in lowering the stress concentration or notch effect at the metal mesh/implant interface since beta titanium alloys are less notch sensitive. The combinations of known acceptable material for use as the implant body, metal mesh and porous surface layer are illustrated in Table I below. t,0060

It should be understood that the metal mesh can be formed in a variety of patterns and is not limited to the grid pattern illustrated in the figures.

It should be also understood that the invention is not to be limited to the precise details above but may be modified within the scope of the appended claims.

I claim:

1. A method of forming an orthopaedic implant having a porous outer coating, said method comprising the steps of:
   a) providing an orthopaedic implant having an outer surface;
   b) forming a plurality of elongate metal beads in a predetermined pattern on the outer surface of the orthopaedic implant, each of said elongate metal beads having an outer surface and being metallurgically bonded to the orthopaedic implant;
   c) providing a porous metal layer; and
   d) metallurgically bonding said porous metal layer to the outer surface of the plurality of elongate metal beads.

2. The method of claim 1 wherein said predetermined pattern is in the form of a mesh.

3. The method of claim 1 wherein the plurality of elongate metal beads may be attached to the surface by a technique selected from the group consisting of arc welding, resistance welding, electron beam welding, laser beam welding, friction welding, ultrasonic welding, and cladding.

4. The method of claim 1 wherein step d includes the step of sintering the porous metal layer to the plurality of elongate metal beads.

5. The method of claim 1 wherein step d includes the step of diffusion bonding the porous metal layer to the plurality of elongate metal beads.

6. The method of claim 1 wherein step b includes the step of shot-peening the implant and the plurality of metal beads.

7. The method of claim 1 wherein step b includes the step of dry blasting the implant and the plurality of metal beads.

8. The method of claim 1 wherein said plurality of elongate metal beads are formed from a material selected from the group consisting of commercially pure titanium, and beta titanium alloys.

9. The method of claim 1 wherein the implant is formed from a material selected from the group consisting of Ti—6Al—4V alloy, beta titanium alloys, and titanium alloys.

10. The method of claim 1 wherein the porous surface layer is formed from any one of the following materials; commercially pure titanium, beta titanium alloys, alpha+beta titanium alloys.

11. An implant constructed in accordance with the method of claim 1 is formed from a material from the group consisting of; Ti—6Al—4V alloy, beta titanium alloys, alpha+beta titanium alloys, and high strength titanium, a layer of metal mesh bonded to the implant, the metal mesh being formed from a material from the group consisting of commercially pure titanium, beta titanium alloys, and alpha+beta titanium alloys, and a porous surface layer metallurgically bonded to the metal mesh, the porous surface layer being formed from a material from the group consisting of commercially pure titanium, beta titanium alloys, and alpha+beta titanium alloys.

* * * * *